(12) United States Patent
Gangakhedkar et al.

(10) Patent No.: US 8,993,739 B2
(45) Date of Patent: Mar. 31, 2015

(54) PROCESS FOR PREPARATION OF KETOLIDE COMPOUNDS

(75) Inventors: Kiran Kumar Gangakhedkar, Aurangabad (IN); Furqan Mohammed Diwan, Aurangabad (IN); Aniruddha Varangaonkar, Aurangabad (IN); Keshav Deo, Aurangabad (IN)

(73) Assignee: Wockhardt Ltd., Bandra-Kurla Complex, Bandra East, Mumbai (IN)

(*) Notice: Subject to any disclaimer, the term of this patent is extended or adjusted under 35 U.S.C. 154(b) by 87 days.

(21) Appl. No.: 14/006,136

(22) PCT Filed: Mar. 12, 2012

(86) PCT No.: PCT/IB2012/051137
§ 371 (c)(1),
(2), (4) Date: Dec. 16, 2013

(87) PCT Pub. No.: WO2012/127351
PCT Pub. Date: Sep. 27, 2012

(65) Prior Publication Data
US 2014/0094600 A1 Apr. 3, 2014

(30) Foreign Application Priority Data
Mar. 22, 2011 (IN) ............... 824/MUM/2011

(51) Int. Cl.
*C07H 17/08* (2006.01)
*C07H 17/00* (2006.01)
(52) U.S. Cl.
CPC ............... *C07H 17/00* (2013.01); *C07H 17/08* (2013.01)
USPC ........................................ 536/7.4

(58) Field of Classification Search
CPC .................................. C07H 17/00; C07H 17/08
See application file for complete search history.

(56) References Cited

FOREIGN PATENT DOCUMENTS

WO    WO 2010/136971 A1    12/2010

*Primary Examiner* — Elli Peselev
(74) *Attorney, Agent, or Firm* — Bio Intellectual Property Services LLC (Bio IPS); O. (Sam) Zaghmout

(57) ABSTRACT

A process for the preparation of compound of Formula (I) is provided. Formula-I

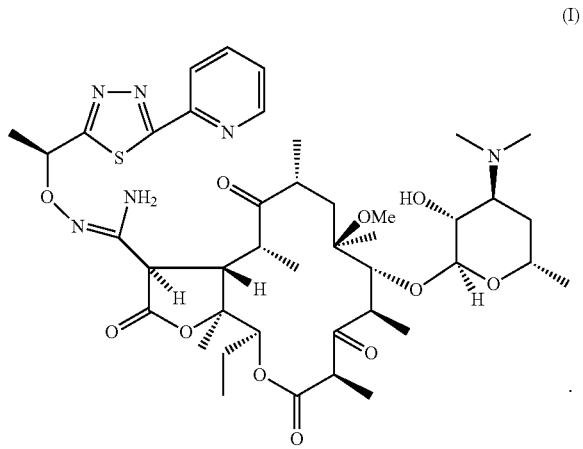

9 Claims, No Drawings

PROCESS FOR PREPARATION OF KETOLIDE COMPOUNDS

FIELD OF THE INVENTION

The invention relates to an improved process for the preparation of ketolide compounds.

BACKGROUND OF THE INVENTION

Macrolides are a well-known family of antimicrobial agents. Erythromycin A, a 14-membered macrolide, was isolated in 1952 from *Streptomyces erythreus*. Examples of macrolides being used as therapeutic agents are roxithromycin, clarithromycin and azithromycin (azalide). Ketolides are semisynthetic 14-membered ring macrolide derivatives, characterized by the presence of a keto function at position 3 instead of L-cladinose moiety present in the macrolactone ring. Telithromycin and Cethromycin are examples of ketolides.

U.S. Pat. No. 4,331,803 discloses 6-O-methyl derivative of erythromycin i.e. Clarithromycin. U.S. Pat. No. 4,349,545 discloses Roxithromycin. The azalide Azithromycin is disclosed in U.S. Pat. No. 4,517,359. Telithromycin is described in EP Patent 680967A1 and corresponding U.S. Pat. No. 5,635,485 and *Bioorg. Med. Chem. Lett.* 1999, 9(21), 3075-3080. Another ketolide Cethromycin (ABT773) is disclosed in WO 98/09978, and *J. Med. Chem.*, 2000, 43, 1045.

In view of the wide use of the macrolide and ketolide compounds as broad-spectrum antimicrobial compounds, there is immense interest in developing these compounds. As can be seen, these compounds are complex chemical compounds with several asymmetric centers, which make their synthesis and purification a difficult task. The present inventors have now surprisingly found an efficient method for synthesizing these compounds in better yields and purity.

SUMMARY OF THE INVENTION

In one general aspect there is provided a process for the preparation of compound of Formula (I)

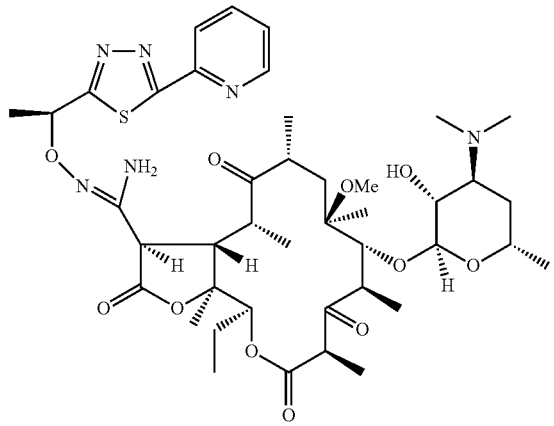

Formula - I

The details of one or more embodiments of the inventions are set forth in the description below. Other features, objects and advantages of the inventions will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise.

In one general aspect, there is provided a process for preparation of compound of Formula (I)

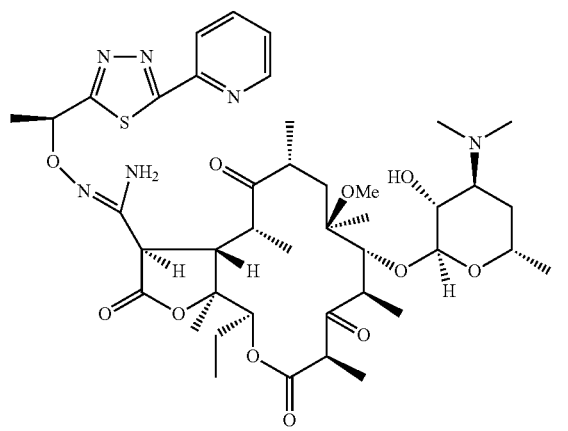

Formula - I comprising, (a) reacting a compound of Formula (II) with a compound of Formula (III) in presence of a base and a protic solvent to obtain a compound of Formula (IV),

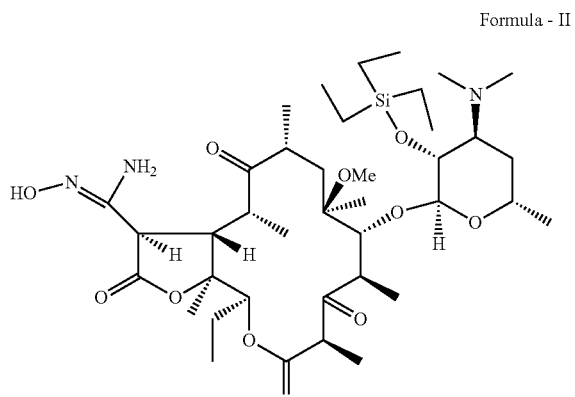

Formula - II

Compound of Formula (IV)

In general, a compound of Formula (IV) is prepared by reacting a compound of Formula (II) with a compound of Formula (III) in presence of a base and a protic solvent.

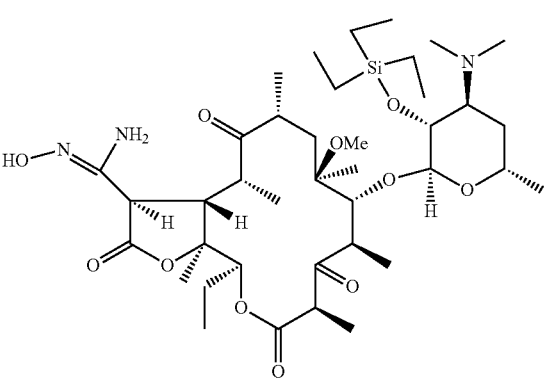

Formula - II

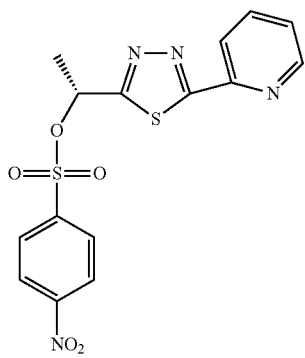

Formula III

A wide variety of bases can be used in this reaction. The base may be an organic base or an inorganic base. Typical, non-limiting examples of inorganic bases include one or more of sodium hydroxide, potassium hydroxide and lithium hydroxide. Typical, non-limiting examples of organic bases include potassium tert-butoxide, sodium methoxide and sodium ethoxide. This reaction is typically carried in presence of a protic solvent. Typical, non-limiting examples of protic solvents include one or more of a $C_1$-$C_6$ alcohol. Suitable, non-limiting examples of $C_1$-$C_6$ alcohols include one or more of methanol, ethanol, n-propanol and iso-propanol.

Compound of Formula (V)

Compound of Formula (V) is obtained by reacting compound of Formula (IV) with N-chlorosuccinimide and dimethylsulfide in presence of a solvent.

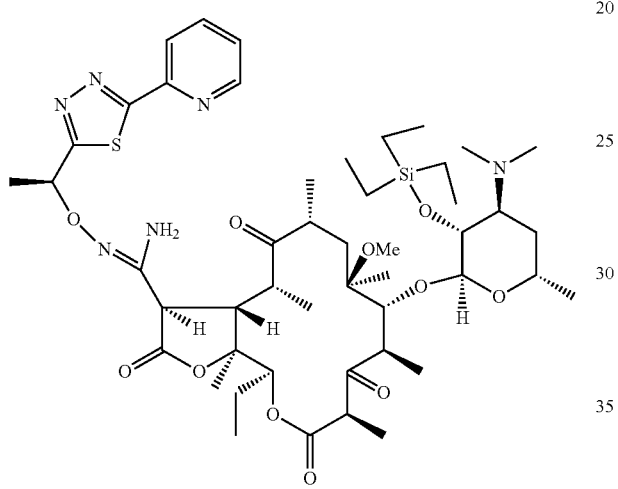

Formula - IV (b) reacting compound of Formula (IV) with N-chlorosuccinimide and dimethylsulfide in presence of a solvent to obtain a compound of Formula (V)

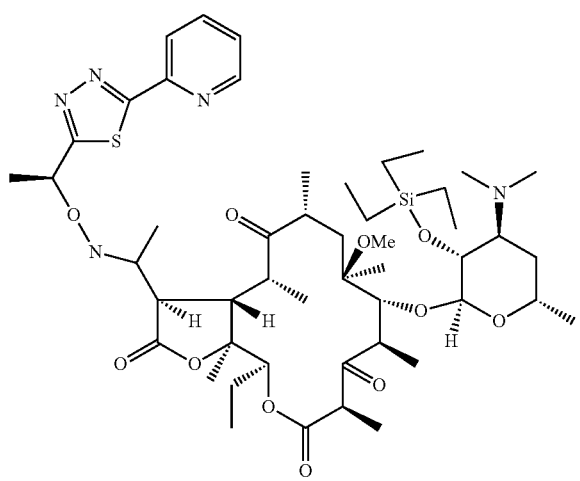

Formula - V (c) de-protecting the silyl-protecting group in compound of Formula (IV) to obtain a compound of Formula (I).

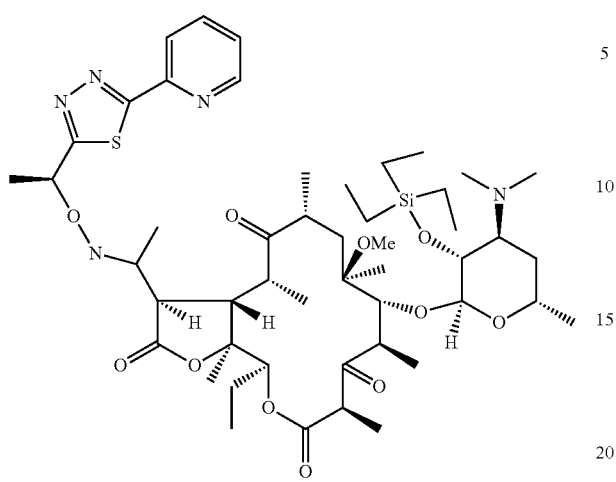

Formula - V

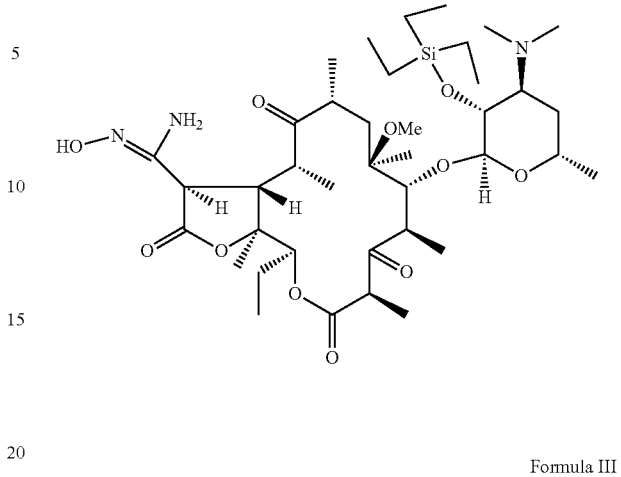

Formula - II

The reaction is typically carried out in presence of solvent. Suitable, non-limiting examples of solvents include non-polar aprotic solvents, chlorinated solvents and mixtures of non-polar aprotic solvents and chlorinated solvents. Typical, non-limiting examples of non-polar solvents include one or more of n-hexane, benzene and toluene. Typical, non-limiting examples of chlorinated solvents include one or more of chloroform, methylene dichloride, ethylene dichloride, and chlorobenzene.

The compound of Formula (V) contains a silyl-protecting group. A compound of Formula (I) is obtained by removing this silyl-protecting group. Typically, such removal is carried out in presence various de-protecting reagents. In one general, non-limiting method, the de-protection of silyl protecting group is achieved by using methanol-water-HCl.

In another general aspect there is provided a process for preparing a compound of Formula (I)

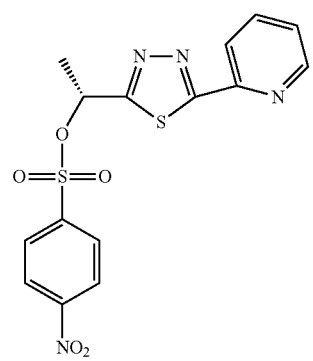

Formula III

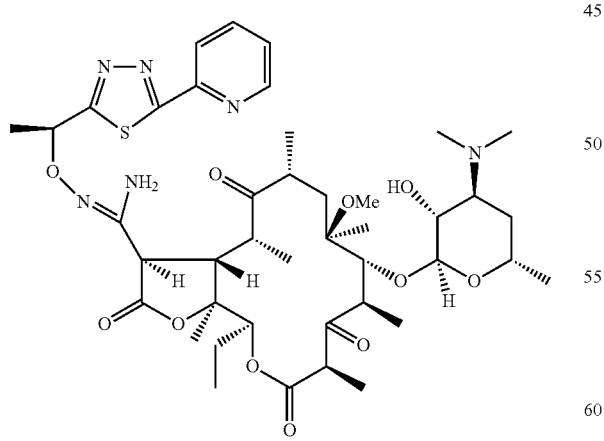

Formula - I

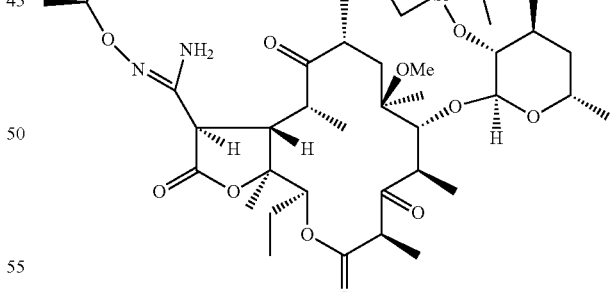

Formula - IV comprising, (a) reacting a compound of Formula (II) with a compound of Formula (III) in presence of an potassium hydroxide and a iso-propanol to obtain a compound of Formula (IV), (b) reacting compound of Formula (IV) with N-chlorosuccinimide and dimethylsulfide in presence of a mixture of toluene and methylene dichloride to obtain a compound of Formula (V)

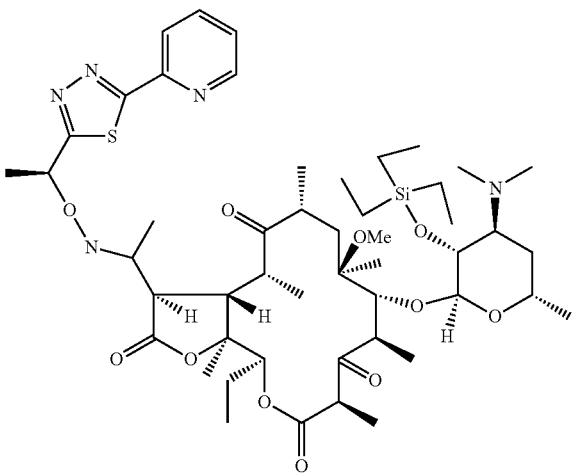

Formula - V (c) de-protecting the silyl-protecting group in compound of Formula (IV) to obtain a compound of Formula (I).

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Synthesis of a Compound of Formula (IV)

1 Kg of a compound of Formula (II) is dissolved in 5 L of iso-propanol. To this solution 0.03 Kg 18-Crown-6, 0.09 Kg of potassium hydroxide and 0.55 Kg of a compound of Formula (III) are added sequentially. The reaction mixture is stirred to completion at 30-45° C. and cooled to room temperature. The reaction is diluted with 5 L of methylene chloride and washed with water and 5% brine. The organic layer is concentrated under reduced pressure and the residue is taken in 5 L methanol and warmed to 45-50° C. 1 L water was added slowly to the solution. The reaction mass was cooled slowly to about 15° C. and stirred for 0.5 h. The precipitated solids were collected by filtration, washed with methanol: water (1:1) and dried to yield 1 Kg (81%) of the compound of Formula (IV). (Purity by HPLC>99%).

Example 2

Synthesis of a Compound of Formula (I)

To a suspension of 0.34 Kg N-Chlorosuccinimide in 7 L mixture of toluene:methylene chloride (4:3) at −5 to −10° C. is slowly added 0.16 Kg dimethylsulfide. The suspension is stirred for 0.5 h at −5 to −10° C. A solution of a compound of Formula (IV) (1 Kg dissolved in 8 L toluene) is added slowly at −10° C. The reaction mass is stirred for 1.5 h and quenched with 0.29 Kg triethylamine. The reaction mass is warmed to 0° C. and stirred for 15 min. The reaction mass is then washed with water, 4% aq. Sodium bicarbonate and water. Organic layer is evaporated to dryness and the residue taken up in 3 L methanol. 2 L~2N HCl is added to the methanolic solution. The reaction mass is stirred to completion of the reaction at ~35° C. The reaction mass is diluted with 2 L water and washed with 3 L×2 toluene. 2 L Methanol is added to the mass and treated with 0.1 Kg activated charcoal for 0.5 h. The charcoal is removed by filtration and the pH of the filtrate is adjusted to 9 with dil.aq.NaOH solution. The precipitate obtained is filtered and washed with 4 L water:methanol. The wet solid is now treated with 5 L methanol at 50° C. for 15 min and subsequently cooled to 25° C. and stirred for 0.5 H. The white solid product is collected by filtration. The wet material is dried to yield 0.75 Kg of a compound of Formula (I) (Purity by HPLC>95%).

We claim:

1. A process for preparing a compound of Formula (I)

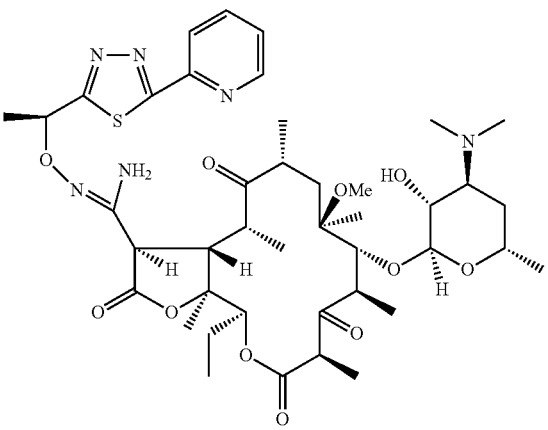

Formula - I comprising, (a) reacting a compound of Formula (II) with a compound of Formula (III) in presence of a base and a protic solvent to obtain a compound of Formula (IV),

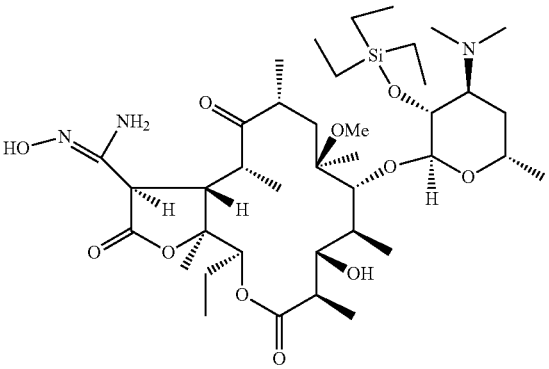

Formula - II

-continued

Formula III

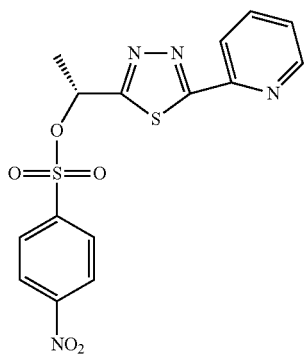

Formula - IV

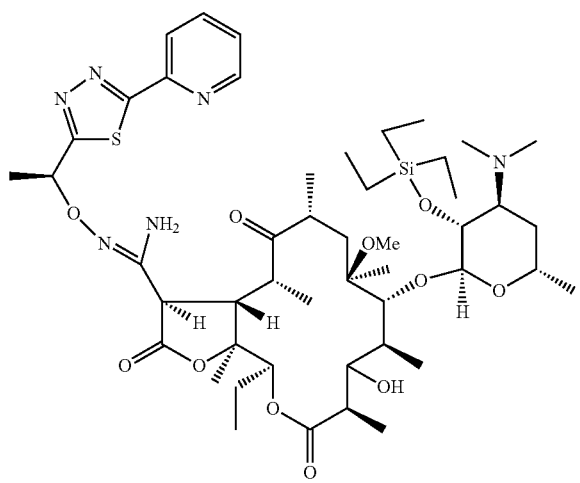

(b) reacting compound of Formula (IV) with N-chlorosuccinimide and dimethylsulfide in presence of a solvent, to obtain a compound of Formula (V):

Formula - V

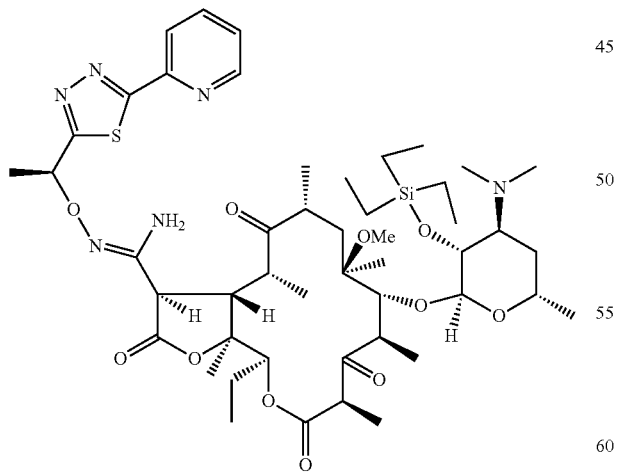

(c) de-protecting the silyl-protecting group in compound of Formula (IV) to obtain a compound of Formula (I).

2. The process according to claim 1, wherein the base used in step (a) is one or more of sodium hydroxide, potassium hydroxide, lithium hydroxide, sodium methoxide, potassium tert butoxide and sodium ethoxide.

3. The process according to claim 1, wherein the protic solvent used in step (a) is a $C_1$-$C_6$ alcohol.

4. The process according to claim 1, wherein the protic solvent used in step (a) is iso-propanol.

5. The process according to claim 1, wherein the solvent used in step (b) is a non-polar aprotic solvent, or a chlorinated solvent, or a mixture of a non-polar aprotic solvent and a chlorinated solvent.

6. The process according to claim 5, wherein the non-polar aprotic solvent is one or more of n-hexane, benzene and toluene.

7. The process according to claim 5, wherein the chlorinated solvent is one or more of chloroform, methylene dichloride, ethylene dichloride, and chlorobenzene.

8. The process according to claim 1, wherein the de-protection of silyl protecting group is achieved by using methanol-water-HCl.

9. A process for preparing a compound of Formula (I)

Formula - I

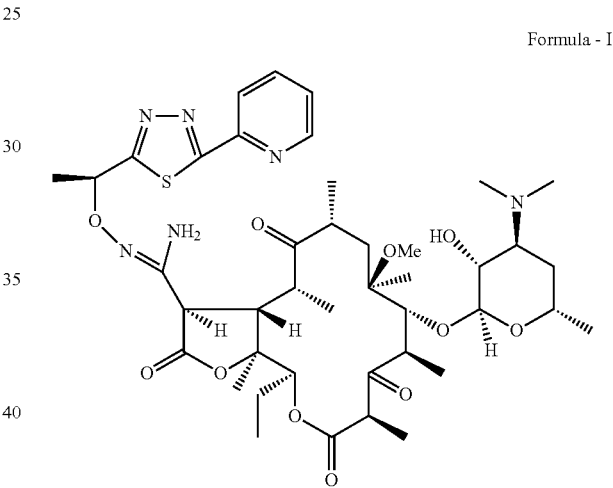

comprising, (a) reacting a compound of Formula (II) with a compound of Formula (III) in presence of potassium hydroxide and a iso-propanol to obtain a compound of Formula (IV), Formula - II

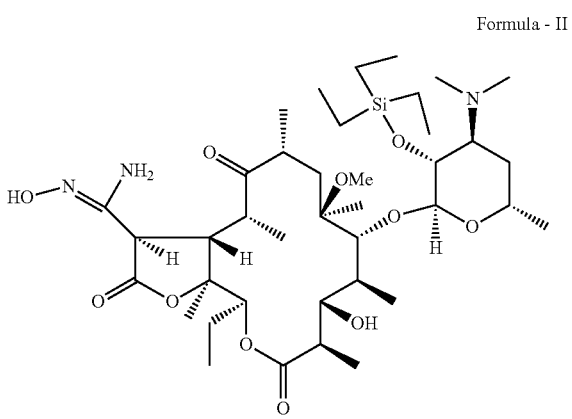

Formula III
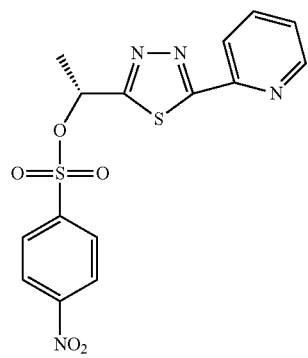
Formula - IV
(b) reacting compound of Formula (IV) with N-chlorosuccinimide and dimethylsulfide in presence of a mixture of toluene and methylene dichloride to obtain a compound of Formula (V)
Formula - V
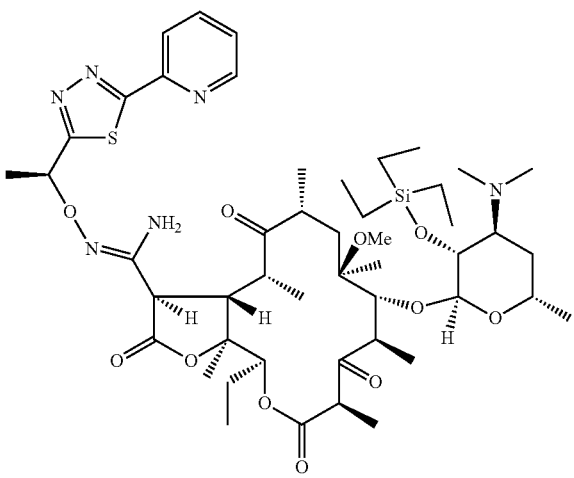
(c) de-protecting the silyl-protecting group in compound of Formula (IV) to obtain a compound of Formula (I).
* * * * *

UNITED STATES PATENT AND TRADEMARK OFFICE
CERTIFICATE OF CORRECTION

PATENT NO. : 8,993,739 B2
APPLICATION NO. : 14/006136
DATED : March 31, 2015
INVENTOR(S) : Kiran Kumar Gangakhedkar et al.

It is certified that error appears in the above-identified patent and that said Letters Patent is hereby corrected as shown below:

IN The Specification

Column 3, lines 66-67, Please replace the following as shown:
"compound of Formula (IV)" with --compound of Formula (V)--

Column 7, lines 22-23, Please replace the following as shown:
"compound of Formula (IV)" with --compound of Formula (V)--

IN The Claims

Column 9, lines 64-65
Claim 1 (in step c): replace the following as shown "compound of Formula (IV)" with --compound of Formula (V)--

Column 10, lines 34-35
Claim 9 (in step c): replace the following as shown "compound of Formula (IV)" with --compound of Formula (V)--

Signed and Sealed this
Fourth Day of August, 2015

Michelle K. Lee
*Director of the United States Patent and Trademark Office*